United States Patent [19]
DeCarlo, Jr. et al.

[11] Patent Number: 6,139,582
[45] Date of Patent: *Oct. 31, 2000

[54] ACETABULAR CUP WITH BI-DIRECTIONAL STEPS

[75] Inventors: Alfred F. DeCarlo, Jr., Stamford, Conn.; Farid Bruce Khalili, Chestnut Hill, Mass.

[73] Assignee: Depuy Orthopaedics, Inc., Warsaw, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/975,604

[22] Filed: Nov. 21, 1997

[51] Int. Cl.⁷ .................................................. A61F 2/34
[52] U.S. Cl. ..................... 623/22.32; 623/22.23
[58] Field of Search ................. 623/22, 23, 18, 623/19, 22.32, 22.23; 606/81, 21

[56] References Cited

U.S. PATENT DOCUMENTS

| | | |
|---|---|---|
| D. 296,714 | 7/1988 | Averill et al. ............................... D24/33 |
| 3,744,061 | 7/1973 | Frost ............................................... 3/1 |
| 3,840,904 | 10/1974 | Tronzo ............................................ 3/1 |
| 3,891,997 | 7/1975 | Herbert ........................................... 3/1 |
| 3,977,026 | 8/1976 | Battault ........................................ 623/22 |
| 4,385,405 | 5/1983 | Teinturier .................................... 623/22 |
| 4,634,444 | 1/1987 | Noiles ......................................... 623/20 |
| 4,662,891 | 5/1987 | Noiles ......................................... 623/22 |
| 4,664,668 | 5/1987 | Beck et al. ................................. 623/23 |
| 4,678,472 | 7/1987 | Noiles ......................................... 623/1.8 |
| 4,695,282 | 9/1987 | Forte et al. ................................. 623/22 |
| 4,704,127 | 11/1987 | Averill et al. ............................... 623/22 |
| 4,795,470 | 1/1989 | Goymann et al. .......................... 623/22 |
| 4,798,610 | 1/1989 | Averill et al. ............................... 623/22 |
| 4,846,839 | 7/1989 | Noiles ......................................... 623/18 |
| 4,865,603 | 9/1989 | Noiles ......................................... 623/18 |
| 4,892,549 | 1/1990 | Figgie, III et al. ......................... 623/22 |
| 4,950,299 | 8/1990 | Noiles ......................................... 623/22 |
| 4,978,356 | 12/1990 | Noiles ......................................... 623/18 |
| 4,997,447 | 3/1991 | Shelley ....................................... 623/22 |
| 5,192,329 | 3/1993 | Christie et al. ............................. 623/22 |
| 5,282,864 | 2/1994 | Noiles et al. ................................ 623/18 |
| 5,290,315 | 3/1994 | DeCarlo, Jr. ............................... 623/22 |
| 5,314,488 | 5/1994 | Hayashi et al. ............................ 623/22 |
| 5,358,532 | 10/1994 | Evans et al. ................................. 623/22 |
| 5,370,704 | 12/1994 | DeCarlo, Jr. ............................... 623/22 |
| 5,413,603 | 5/1995 | Noiles et al. ................................ 623/18 |
| 5,458,649 | 10/1995 | Spotorno et al. .......................... 623/22 |
| 5,549,694 | 8/1996 | Noiles et al. ................................ 623/22 |
| 5,549,697 | 8/1996 | Caldarise .................................... 623/22 |
| 5,549,698 | 8/1996 | Averill ......................................... 623/22 |
| 5,549,701 | 8/1996 | Mikhail ....................................... 623/22 |
| 5,571,201 | 11/1996 | Averill et al. ............................... 623/22 |
| 5,676,704 | 10/1997 | Ries et al. .................................... 623/18 |
| 5,735,901 | 4/1998 | Maumy et al. .............................. 623/18 |
| 5,755,799 | 5/1998 | Oehy et al. .................................. 623/18 |
| 5,928,288 | 7/1999 | Wilson ........................................ 623/22 |

FOREIGN PATENT DOCUMENTS

| | | | |
|---|---|---|---|
| 0285756 | 10/1988 | European Pat. Off. ................. | 623/22 |
| 2639822 | 6/1990 | France ....................................... | 623/22 |
| 3049219 | 7/1982 | Germany ................................... | 623/22 |
| 0858817 | 8/1981 | U.S.S.R. .................................... | 623/22 |

*Primary Examiner*—Bruce Snow
*Attorney, Agent, or Firm*—Nutter, McClennen & Fish, LLP

[57] ABSTRACT

An acetabular cup having an outer surface with a first set of steps formed in a first direction and a second set of steps formed in a different, second direction is effective to provide positional stability and enhanced load transfer after implantation in the acetabulum. The stepped outer surface of the acetabular cup provides a significant increase in effective surface area. The multi-directional first and second steps convert shear loads to compressive loads in their respective directions, resulting in enhanced fixation of the cup.

15 Claims, 5 Drawing Sheets

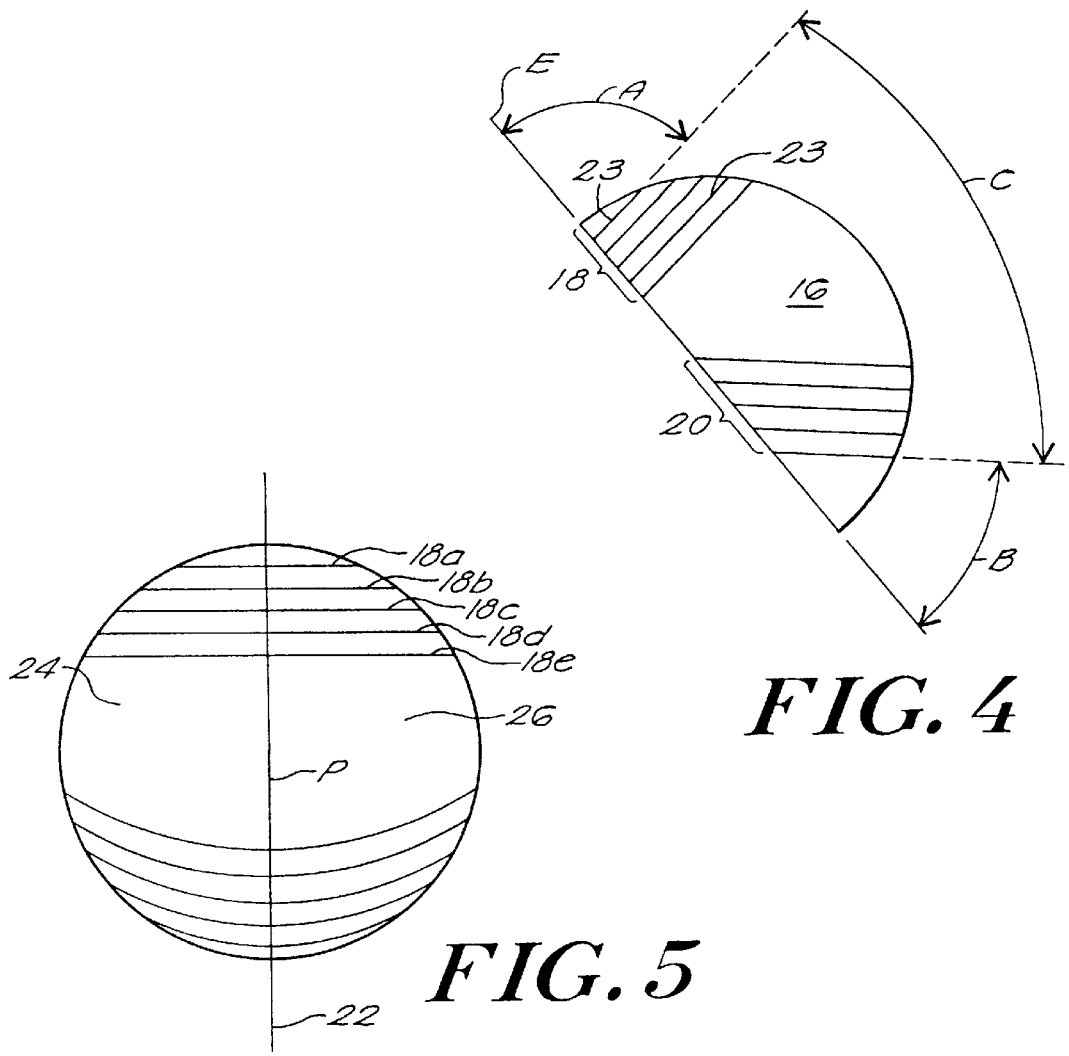
FIG. 4
FIG. 5
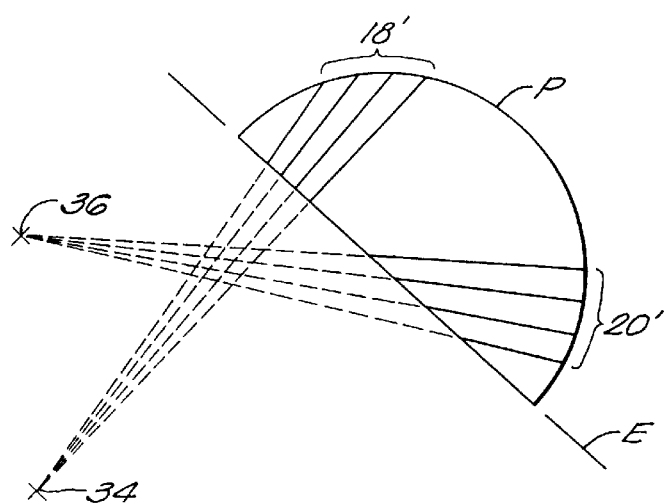
FIG. 6

ACETABULAR CUP WITH BI-DIRECTIONAL STEPS

CROSS REFERENCE TO RELATED APPLICATION

Not Applicable.

STATEMENT REGARDING FEDERALLY SPONSORED RESEARCH

Not Applicable.

BACKGROUND OF THE INVENTION

The invention relates generally to prosthetic components used in joint arthroplasty, and more particularly to an acetabular cup having enhanced fixation properties within the acetabulum of a patient.

Joint arthroplasty is a well known surgical procedure by which a diseased and/or damaged natural joint is replaced by a prosthetic joint. Joint arthroplasty is commonly performed for hips, knees, elbows, and other joints. The health and condition of the joint to be replaced dictate the type of prosthesis necessary to replace the natural joint. For example, in a total hip arthroplasty an acetabular cup is implanted in the acetabular cavity in the pelvis to replace the natural acetabulum. Replacement of the acetabulum is necessary when there is an inadequate articulation surface for a head or ball of a prosthetic femoral component.

To implant an acetabular cup, a cavity is reamed in the acetabulum. The reamed cavity generally conforms to an outer surface of the acetabular cup. The acetabular cup is then inserted into the formed cavity and secured by mechanical means, interference fit, or by a combination thereof. The acetabular cup is positioned in the pelvis at a fixed orientation with respect to patient anatomy and should remain stable.

Movement of the implanted acetabular cup over time can erode the surrounding bone of the acetabular cavity. The effect of such bone erosion is the loosening of the acetabular cup, allowing it to shift in position. Positional displacement of the acetabular cup with respect to the acetabulum can lead to dislocation of the joint.

Acetabular cup displacement can also generate excessive wear debris in which particulate material, which can interfere with joint articulation, is present within the joint. As the acetabular cup moves with respect to the pelvis, the implanted femoral head may no longer articulate in the acetabular cup within a desired range of motion. Improper positioning of the femoral head with respect to the acetabular cup can also accelerate the generation of wear debris creating a need for revision surgery.

Revision procedures in which the acetabular cup is replaced with a new prosthesis pose challenges as the replacement acetabular cup must be securely implanted in the pelvis. Bone erosion that typically necessitates such a revision procedure often produces an acetabular cavity having an elongated shape that does not provide the most favorable conditions for an interference fit with many acetabular cups. Although bone grafts can be effected to reshape the acetabular cavity to be generally hemispherical, there are certain drawbacks to such bone grafts. For example, a suitable graft bone may not be readily available, it may be difficult to secure the bone graft to the existing bone, and the graft material may not provide sufficient mechanical strength.

Various methods and techniques are presently used to secure an acetabular cup in a cavity formed in the acetabulum of a patient. One such method includes the use of bone cement to secure the acetabular cup to the acetabulum. Another technique utilizes an acetabular cup having holes for receiving screws, or other such fasteners, to affix the acetabular cup to bone.

Acetabular cups with a variety of external geometries are known in the art. For example, U.S. Pat. No. 5,571,201 (Averill et al.) discloses an acetabular cup having a plurality of unidirectional steps for engaging bone. U.S. Pat. No. 5,358,532 (Evans et al.) discloses an acetabular cup having a plurality of parallel annular rings disposed about an outer surface of the acetabular cup. The rings extend from a rim portion of the cup in a direction towards the apex of the cup. U.S. Pat. Nos. 4,662,891 (Noiles) and 5,413,603 (Noiles et al.) also disclose acetabular cups with stepped outer surfaces.

Although, such acetabular cups are able to achieve some degree of fixation to the acetabulum of a patient, an acetabular cup is desired that more effectively remains affixed in the acetabular cavity to reduce the likelihood of joint dislocation, minimize wear debris, and avoid revision surgery.

SUMMARY OF THE INVENTION

The present invention provides an acetabular cup having enhanced bone fixation and securement properties. In one embodiment, the acetabular cup has an outer surface with first and second sets of steps formed thereon, wherein each of the first and second sets of steps extend in different directions. Although the invention is applicable to a variety of joint prostheses, it is primarily described in conjunction with an acetabular cup.

The acetabular cup of the invention includes a concave inner surface and a convex outer surface. First and second sets of steps are formed on the outer surface of the acetabular cup for engaging bone to prevent or minimize any migration of the acetabular cup once it is implanted within the acetabulum. As noted above, the first and second steps are formed in different directions to provide significant surface area that is optimized to resist dislocation forces and to distribute loads on the hip joint. In one embodiment, the first set of steps is formed on a superior portion of the shell while the second set of steps is formed on an inferior portion of the shell.

To implant the acetabular cup, a cavity is reamed in the acetabulum of a patient and the acetabular cup is impacted into the formed cavity and secured therein by means of an interference fit. The first and second steps formed on the outer surface of the acetabular cup engage the bone and secure the acetabular cup in position. The steps provide stable fixation of the acetabular cup and effectively transfer load to the acetabulum to reduce or eliminate bone resorption. Ideally, the first set of steps, formed on the superior portion of the shell, resist forces that would tend to cause superior migration of an implanted acetabular shell. The second set of steps, formed on the inferior part of the shell, resist forces that would tend to cause medial migration of an implanted shell.

BRIEF DESCRIPTION OF THE DRAWINGS

The invention will be more fully understood from the following detailed description taken in conjunction with the accompanying drawings, in which:

FIG. 4 is a side view of the acetabular cup of FIG. 1;

FIG. 5 is a top view of the acetabular cup of FIG. 1;

FIG. 6 is a side view of an alternative embodiment of an acetabular cup according to the present invention;

DETAILED DESCRIPTION OF THE INVENTION

Figure 1:
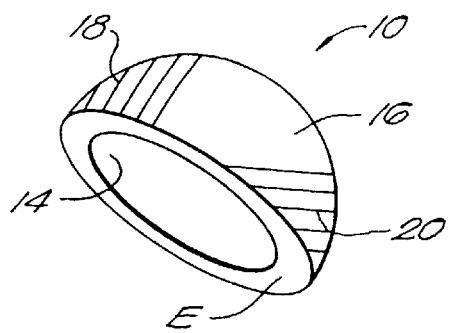
FIG. 1 is a perspective view of an acetabular cup in accordance with the present invention.

The present invention provides an implantable joint prosthesis that offers enhanced fixation properties to maintain positional stability of the prosthesis over time. The invention is particularly applicable to acetabular cups. For purposes of illustration, the present invention is described herein with reference to an acetabular cup suitable for implantation within an acetabular cavity of a patient. It is understood, however, that the invention can be adapted for use with a variety of joint prostheses.

FIGS. 1–5 illustrate an exemplary acetabular cup 10 according to the present invention, that is suitable for implantation in the acetabulum 12 of a patient. The acetabular cup 10 includes a concave inner surface 14 and a convex outer surface 16 with a first set of steps 18 and a second set of steps 20 formed on the outer surface 16. The first set of steps 18 extend in a first direction and the second set of steps 20 extend in a second direction different from the first direction. The first and second sets of steps 18,20 engage the acetabulum 12 at the cup/bone interface to distribute a load on the joint and to resist displacement of the acetabular cup 10 after it is implanted within the acetabulum.

Although the invention is described herein as having first and second sets of steps, it is understood that more than two sets of steps can be formed on the outer surface of the acetabular cup, and the steps can extend in a plurality of directions.

The acetabular cup 10 has a pole P, at a top portion of its outer surface, and an equator region E opposite the pole P. Further, the acetabular cup 10 is divided by a first plane 22 (FIG. 5) into an anterior portion 24 and a posterior portion 26. A second plane 28 (FIG. 2) divides the acetabular cup 10 into a superior portion 30 and an inferior portion 32.

The first set of steps 18 is formed in the superior portion 30 of the outer surface 16 of the acetabular cup. First steps 18 typically extend from the anterior portion 24 to the posterior portion 26 of cup 10. Although shown as extending from a first point on the equator region E to a second point thereon, it is understood that the steps may extend from a point on the outer surface 16 disposed above the equatorial plane E (i.e., toward the pole P).

As shown in FIG. 4, the first steps 18 form an angle A with respect to the equatorial plane E. The angle is less than or equal to 90 degrees, and typically is in the range of 75 to 90 degrees.

The second set of steps 20 is formed on the inferior portion 32 of the acetabular cup. Typically, steps 20 extend from the anterior portion 24 to the posterior portion 26 of the cup 10. The second steps 20 form an angle B with respect to the equator E. The angle B can vary from about 0 degrees to about 45 degrees, and typically is about 20 degrees.

The first and second steps 18,20 form an angle C with respect to each other that can range from about 35 degrees to about 95 degrees. In one embodiment, the angle C formed between the first and second set of steps is about 60 degrees.

The orientation of the individual steps that form the first and second steps 18,20 can be the same with respect to each other, or it can vary. The steps can be substantially parallel with respect to each other, or they can vary in a radial, parabolic, and hyperbolic relationship.

In the exemplary embodiment of FIG. 5, each of the steps 18a–e that form the first set of steps 18 are substantially parallel to each other. In the embodiment shown in FIG. 6, the steps 18' are radially disposed about the convex outer surface. That is, the steps 18' extend radially along the outer surface from a point 34 located on or at a distance from the equator E.

Figure 2:
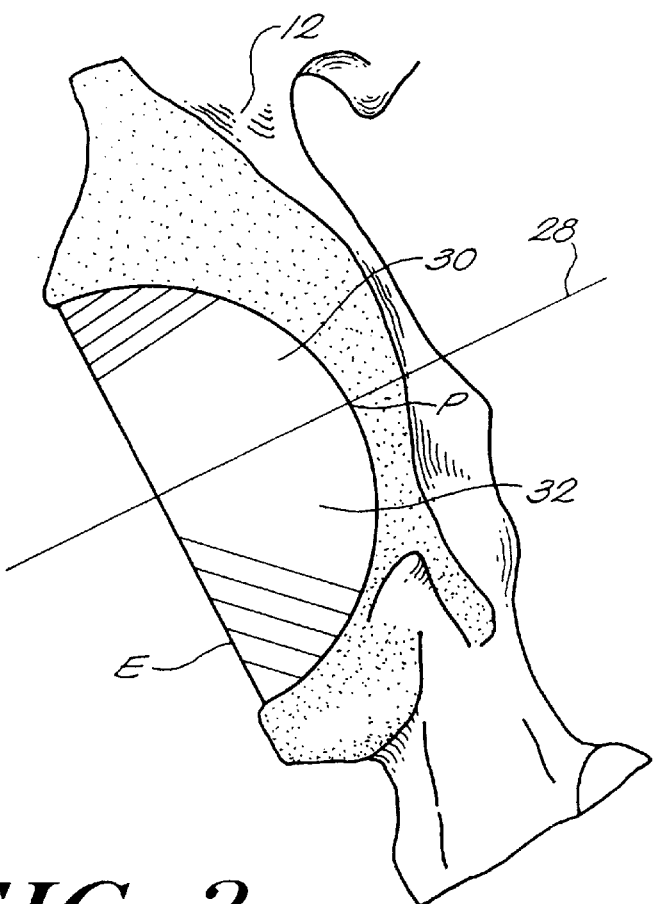
FIG. 2 is a side view of the acetabular cup of FIG. 1 shown implanted in an acetabulum.

Similarly, the second set of steps 20 can be parallel as shown in FIG. 2. Alternatively, the second steps 20' can extend radially from a point 36, as shown in FIG. 6. The points 34,36 can be located on or at a selected distance from the equator E. It is understood, however, that one or more of the steps can extend from more than one such point. That is, the radial relationship of the steps 20' can vary from step to step since the steps can extend from different points.

In another embodiment, the first set of steps 18 may extend parallel to each other and the second set of steps 20' may extend radially along the outer surface of the acetabular cup.

Figure 7:
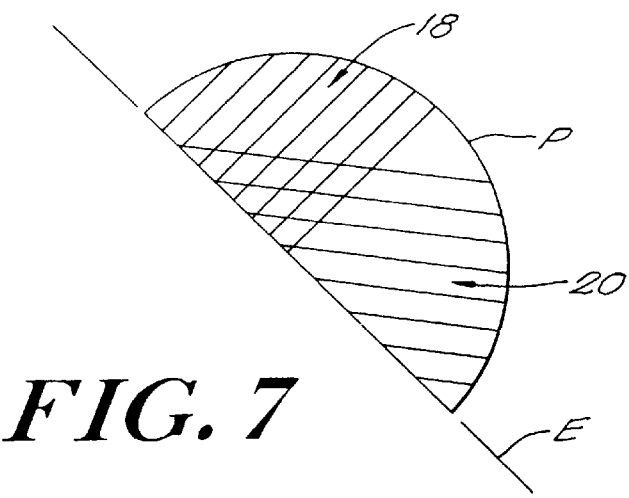
FIG. 7 is a side view of a further embodiment of an acetabular cup according to the present invention.

The first set of steps 18 are formed generally on the superior portion 30 of the outer surface 16 of the acetabular cup. Nevertheless, the first set of steps 18 may extend, to some degree, into the inferior portion 32 of the acetabular cup as well. In a preferred embodiment, the steps 18 do not extend beyond the pole region P which delineates the superior 30 and inferior 32 portions of the acetabular cup. Similarly, the second set of steps 20 predominantly are formed on the inferior portion 32 of the acetabular cup, but they can also be formed on the superior portion 30. In the embodiment of FIG. 7, the first and second set of steps 18,20 overlap each other, with the second set of steps 20 extending into the superior portion 30 of the acetabular cup.

The steps 18,20 can be formed in a variety of geometries. The steps can be formed in a continuous manner along the outer surface of the acetabular cup, or they can be formed from discrete portions. The steps can be linear or they can be arcuate or wavy. Further, a crest of the steps can be constant height or can undulate so that the crest of the steps varies in a pattern or in a random manner. Also, each crest can form a single edge or can comprise a series of edges. The steps can extend above the outer surface or they can be recessed below the outer surface. In the embodiments illustrated in FIGS. 1–10, the steps 18,20 are continuous across the outer surface 16 of the acetabular cup.

Figure 3:
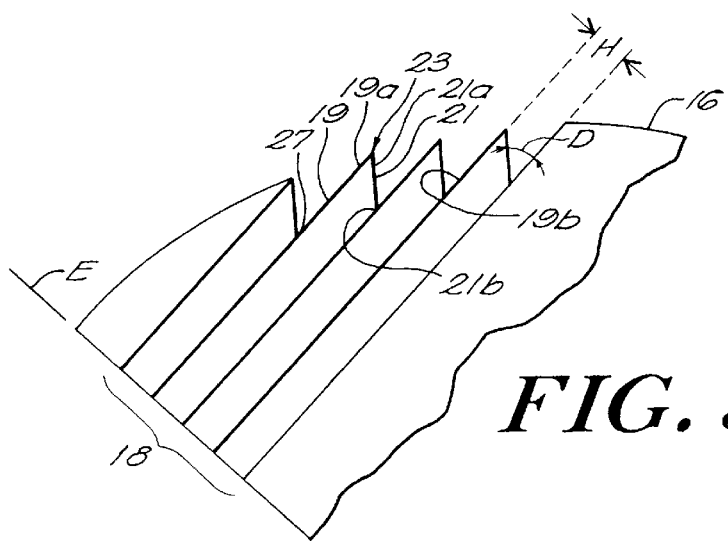
FIG. 3 is a partially cut-away, detailed side view of a portion of the acetabular cup of FIG. 1.

In the embodiment illustrated in FIG. 3, each step 18 has a superior surface 19 and an inferior surface 21. An end portion 19a of superior surface 19 joins an end portion 21a of inferior surface 21 to form a crest 23. Similarly a rear portion 19b of superior surface 19 joins a rear portion 21b of inferior surface 21 to form groove 27.

One of ordinary skill in the art will appreciate that the steps 18,20 can be defined by various parameters. For example, the angle D formed by the superior surface 19 and the inferior surface 21 can vary from about 5 degrees to about 175 degrees. Preferably, angle D is in the range of about 45 degrees to 120 degrees, and most preferably it is about 90 degrees. The height H of the steps 18 can range from about 0.25 millimeter to about 3.00 millimeters, and is preferably about 1.50 millimeters.

Figure 3A:
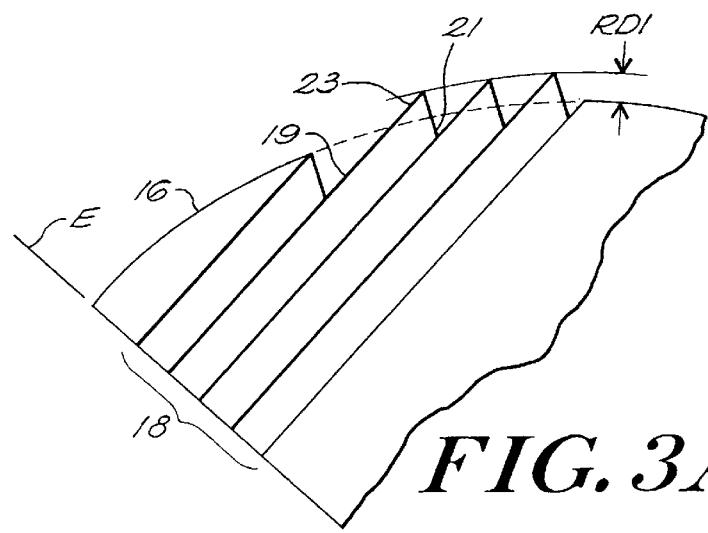
FIG. 3A is a side view of a another embodiment of the acetabular cup of FIG. 3.
Figure 3B:
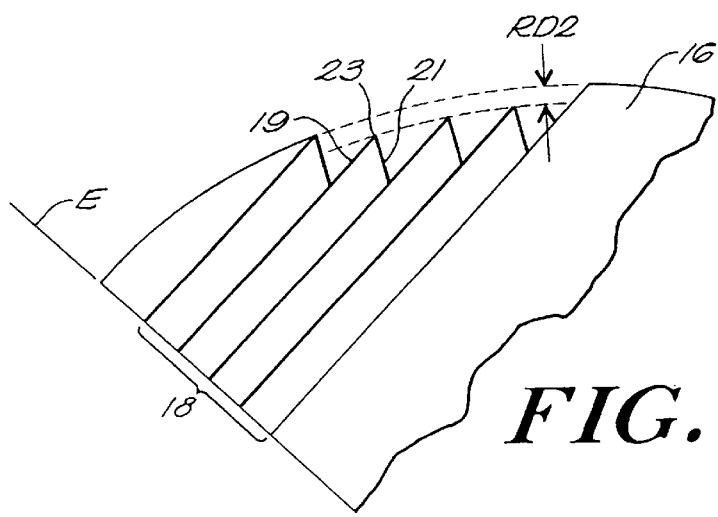
FIG. 3B is a side view of further embodiment of the acetabular cup of FIG. 3.

In another embodiment shown in FIG. 3A, the crests 23 of the steps 18 extend a radial distance RD1 beyond the outer surface 16 of the acetabular cup. In a further embodiment shown in FIG. 3B, the crests 23 are recessed a radial distance RD2 below the outer surface 16.

Further, the number and spacing of the steps 18,20 formed on the acetabular cup can vary in relation to the condition of the acetabulum, the size of the acetabular cup, and the desired step pitch. The number of steps or rows that comprise the first set of steps 18 can vary from about 2 to about 20 steps and the second set of steps 20 can have from about 2 to about 20 steps or rows. In an exemplary embodiment, the first and second set of steps 18,20 each have about seven steps or rows.

The first and second sets of steps 18,20 formed on the outer surface 16 of the acetabular cup provide secure fixation in the acetabulum thereby increasing the useful life of the implant. As described below, the first and second steps 18,20 provide a bone-friendly interface between the bone and the implanted acetabular cup and provide significant surface area to distribute load on the joint. The steps 18,20 also provide a taper lock effect that resists migration of the implanted acetabular cup. The first steps 18 are believed to be effective to resist superior migration of the implanted acetabular cup into the acetabulum while the second steps 20 are believed to resist medial migration. The cumulative effect of the presence of steps 18, 20 is to normalize interface shear loads caused by major joint loads that result from normal daily activities.

Figure 10:
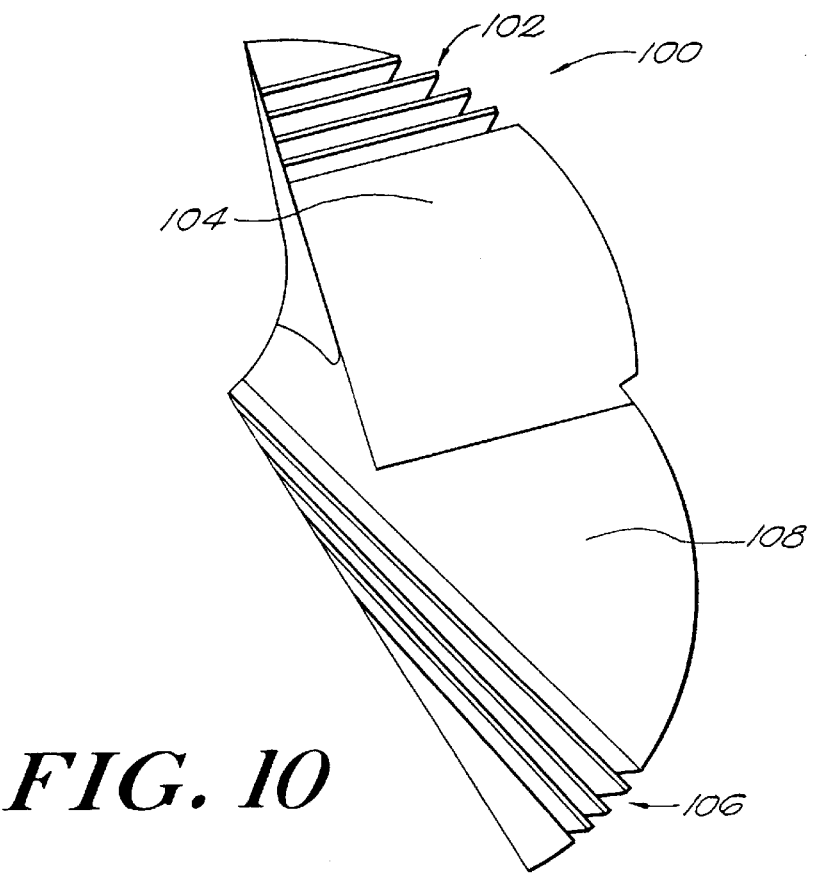
FIG. 10 is a side view of another embodiment of an acetabular cup according to the present invention.

FIG. 10 illustrates another embodiment of an acetabular cup 100 in which the cup is elongated in the superior/inferior direction to fit within an elongated acetabular cavity. The acetabular cup 100 has a first set of steps 102 formed on a superior portion 104 of the acetabular cup and a second set of steps 104 formed on an inferior portion 106. The first and second steps 102,106 are formed in different directions to provide multi-directional load distribution and significant increase in surface area for diffusion of a load.

To implant the acetabular cup, one or two spherical cavities are reamed in the acetabulum of a patient. The overall peripheral dimensions of the formed cavity is slightly smaller than that of the acetabular cup, measured at the equator E. The acetabular cup is then forced into the cavity and secured therein by means of an interference fit.

The steps 18, 20 are located on the outer surface of the acetabular cup such that they convert shear loads on the interface (which are caused by daily activities) to compressive loads. Clinical history has shown that cancellous bone can better tolerate compressive loads as compared to shear loads. By maintaining a compressive load, the device is believed to minimize bone resorption, and the bone structure is then better able to prevent migration of the acetabular cup into the formed acetabular cavity.

Figure 8B:
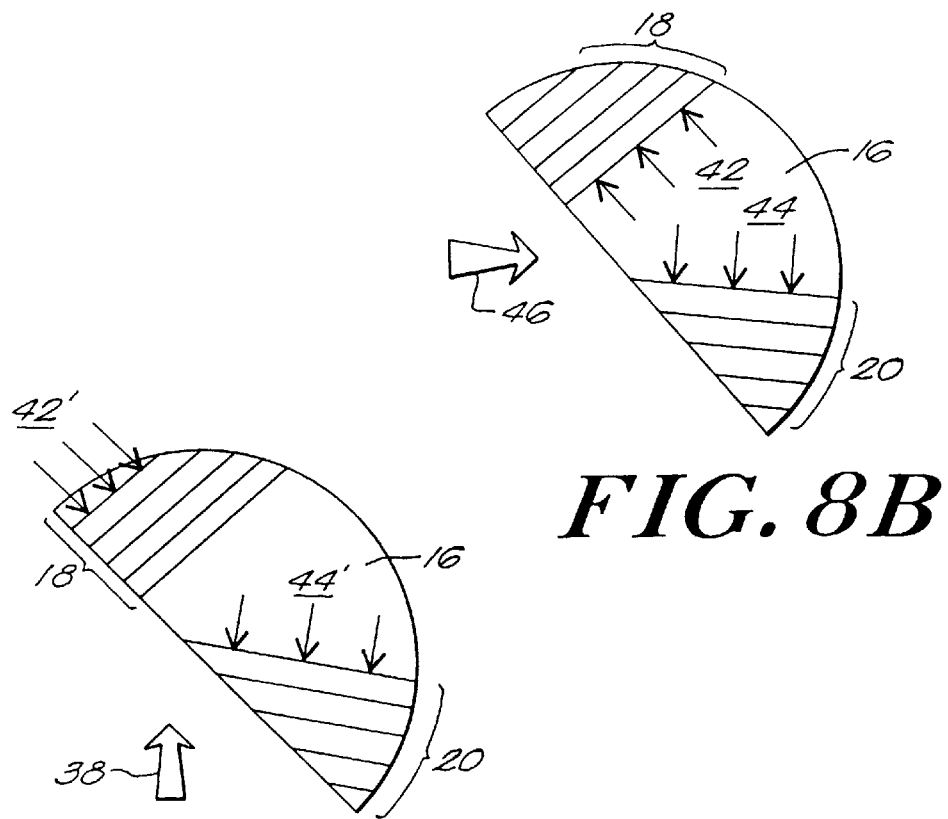
FIG. 8B is a side view of the acetabular cup according to the present invention showing a medial load on the acetabular cup.
Figure 8A:
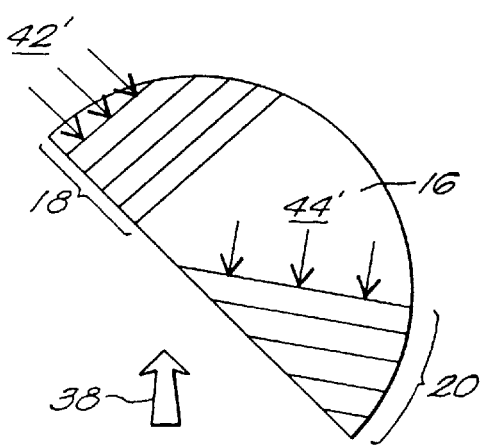
FIG. 8A is a side view of the acetabular cup according to the present invention showing a superior load on the acetabular cup.
Figure 9:
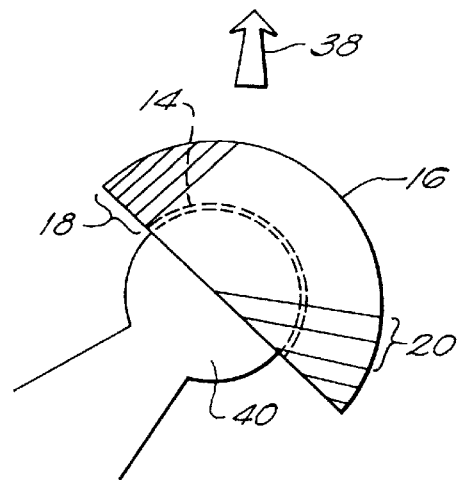
FIG. 9 is a side view of the acetabular cup according to the present invention showing a femoral head disposed within the acetabular cup.

FIGS. 8A and 9 show a load 38 on the implanted acetabular cup bearing on the cup (and joint) in a superior direction. This superior load 38 is borne by the inner surface 14 of the acetabular cup, a femoral head 40 disposed therein, and the outer surface 16 and the acetabulum 12 (FIG. 2). The load 38 is distributed about the first steps 18 as indicated by first arrows 42 and about the second steps 20 as indicated by second arrows 44. The load 38 is thus distributed in multiple directions about the surface area provided by the steps 18,20. The first and second steps 18,20 resist migration of the implanted acetabular cup in the presence of loads, such as the superior load 38.

Similarly, FIG. 8B shows a generally medial load 46 distributed about the first and second steps 18,20 as indicated by arrows 42',44'. The medial load 46 is resisted by the first and second steps 18,20 to prevent displacement of the acetabular cup with respect to the acetabulum.

The joint is subjected to loads in other directions as well. For example, during squatting, or similar motions, the hip joint bears loads in a posterior/medial direction. The first and second steps 18,20 resist loads in their respective directions to withstand loading of the joint in a range of directions and prevent displacement of the implanted acetabular cup.

One of ordinary skill in the art will appreciate that the acetabular cup of the present invention can be made from a variety of biocompatible materials having high strength and durability. Examples of such materials include metal alloys as titanium alloys, cobalt chromium alloys, and stainless steel.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An acetabular cup for implantation in an acetabulum of a patient, comprising;

a shell component having a generally convex outer surface;

a first plurality of rigid, spaced steps formed on a first portion of the outer surface of the shell component having crests extending in a first direction, the first plurality of steps being effective to engage bone for affixing the acetabular cup in the patient's acetabulum, the first plurality of steps extending from points on or near an equator of the convex outer surface of the shell component to points on or near the equator, at least one step in the first plurality of steps intersecting a plane that is generally parallel to the equator and equidistant to the equator and a pole of the shell component;

a second plurality of rigid, spaced steps formed on a second portion of the outer surface of the shell component having crests extending in a second direction different from the first direction, the second plurality of steps being effective to engage bone for affixing the acetabular cup in the patient's acetabulum, the second plurality of steps extending from or near the equator of the convex outer surface of the shell component, said first and second sets of spaced steps being angled to normalize interface shear load caused by major joint loads during daily activity and resist superior and medial migration of the shell.

2. The acetabular cup according to claim 1, wherein at least some of the first plurality of steps are parallel with respect to each other.

3. An acetabular cup, comprising:

a generally hemispherical shell having an anterior portion, a posterior portion, a superior portion and an inferior portion, such that a first plane bisects the shell to partition the anterior and posterior portions and a second plane, which is generally perpendicular to the first plane, bisects the shell to partition the superior and inferior portions, the shell further including a concave inner surface and a convex outer surface which meet at an equator, the shell further including a third plane generally parallel to the equator such that the third plane is substantially equidistant between the equator and a pole of the shell outer surface;

a first set of spaced steps formed on the outer surface of the superior portion of the shell for engaging bone to secure the acetabular cup in an acetabular cavity, the first set of steps having crests extending in a first direction, wherein at least one step in the first set of steps extends from a point on or proximate the equator in the anterior portion of the shell, such that it intersects the third plane, to a point on or proximate the equator in the posterior portion of the shell; and a second set of spaced steps formed on the outer surface of the shell for engaging bone to secure the acetabular cup in the acetabular cavity, the second set of steps having crests extending in a second direction different than the first direction, wherein at least one step in the second set of steps extends from a point on or proximate the equator, said first and second sets of spaced steps being angled to normalize interface shear load caused by major joint loads during daily activity and resist superior and medial migration of the shell.

4. The acetabular cup according to claim 3, wherein at least one of the steps in the first and second set of steps has a superior surface and an inferior surface that intersect to form the step crest.

5. The acetabular cup according to claim 4, wherein the inferior surface and the superior surface form an angle of between about 45 degrees and about 120 degrees.

6. The acetabular cup according to claim 1, wherein the first set of steps do not extend to the inferior portion of the shell.

7. The acetabular cup according to claim 3, wherein the second set of steps are at least partially disposed on the inferior portion of the shell.

8. The acetabular cup according to claim 3, wherein the first set of steps form an angle in the range of about 75 to 90 degrees with respect to the equator.

9. The acetabular cup according to claim 3, wherein the first set of steps form an angle of less than or equal to about ninety degrees with respect to the equator.

10. The acetabular cup according to claim 3, wherein the second set of steps form an angle of between 0 and 45 degrees with respect to the equator.

11. The acetabular cup according to claim 3, wherein the first set of steps and the second set of steps form an angle ranging from about 35 to about 90 degrees with respect to each other.

12. The acetabular cup according to claim 3, wherein at least one step in the first set of steps is parallel to at least one other step in the first set of steps.

13. The acetabular cup according to claim 3, wherein at least one step in the second set of steps is parallel to at least one other step in the second set of steps.

14. The acetabular cup according to claim 3, wherein the first set of steps includes from about 2 to about 20 steps.

15. The acetabular cup according to claim 3, wherein the second set of steps includes from about 2 to about 20 steps.

* * * * *